(12) United States Patent
Sørensen et al.

(10) Patent No.: US 11,766,163 B2
(45) Date of Patent: Sep. 26, 2023

(54) TIP PART FOR AN ENDOSCOPE AND THE MANUFACTURE THEREOF

(71) Applicant: Ambu A/S, Ballerup (DK)

(72) Inventors: Morten Sørensen, Ballerup (DK); Jan Guldberg Hansen, Greve (DK)

(73) Assignee: AMBU A/S, Ballerup (DK)

( * ) Notice: Subject to any disclaimer, the term of this patent is extended or adjusted under 35 U.S.C. 154(b) by 29 days.

(21) Appl. No.: 17/032,535

(22) Filed: Sep. 25, 2020

(65) Prior Publication Data

US 2021/0093175 A1 Apr. 1, 2021

(30) Foreign Application Priority Data

Sep. 26, 2019 (EP) ..................... 19199924

(51) Int. Cl.
| | |
|---|---|
| *A61B 1/00* | (2006.01) |
| *A61B 1/05* | (2006.01) |
| *A61B 1/018* | (2006.01) |
| *A61B 1/07* | (2006.01) |
| *A61B 1/005* | (2006.01) |
| *A61B 1/06* | (2006.01) |

(52) U.S. Cl.
CPC ........ *A61B 1/00103* (2013.01); *A61B 1/0008* (2013.01); *A61B 1/009* (2022.02); *A61B 1/0011* (2013.01); *A61B 1/018* (2013.01); *A61B 1/051* (2013.01); *A61B 1/07* (2013.01); *A61B 1/0684* (2013.01)

(58) Field of Classification Search
CPC ....... A61B 1/051; A61B 1/0011; A61B 1/005; A61B 1/018; A61B 1/07; A61B 1/0684; A61B 1/00103; A61B 1/00096; A61B 1/126; A61B 1/00071; A61B 1/00142; A61B 1/00165; A61B 1/04; G02B 1/18; G02B 23/2423; G02B 27/0006; G02B 1/16
USPC ......................................... 600/133
See application file for complete search history.

(56) References Cited

U.S. PATENT DOCUMENTS

| | | |
|---|---|---|
| 4,580,551 A | 4/1986 | Siegmund et al. |
| 4,651,718 A | 3/1987 | Collins |
| 4,706,653 A | 11/1987 | Yamamoto |
| 4,745,470 A | 5/1988 | Yabe et al. |

(Continued)

FOREIGN PATENT DOCUMENTS

| | | |
|---|---|---|
| EP | 2 387 346 B1 | 8/2015 |
| EP | 3539449 A1 | 9/2019 |
| WO | WO 2014/106511 A1 | 7/2014 |

OTHER PUBLICATIONS

Chris Tensen, Alexander B. et al., "Injection moulding of antireflective nanostructures", Microelectronic Engineering 121 (2014) 47-50.

(Continued)

*Primary Examiner* — John P Leubecker
(74) *Attorney, Agent, or Firm* — Faegre Drinker Biddle & Reath LLP

(57) ABSTRACT

A tip part (2) for an endoscope (1) having at least one transparent part and at least one opaque part providing an outer surface. The outer surface comprises a transparent outer surface part (6, 7) and an opaque outer surface part (9, 10), respectively. The transparent outer surface part is smooth (6, 7) and at least a part of the opaque outer surface part (9, 10) is provided with a hydrophobic structure.

17 Claims, 6 Drawing Sheets

(56) References Cited

U.S. PATENT DOCUMENTS

| | | | |
|---|---|---|---|
| 4,778,247 A | 10/1988 | Carpenter | |
| 4,832,003 A | 5/1989 | Yabe | |
| 4,856,495 A | 8/1989 | Tohjoh et al. | |
| 4,860,732 A | 8/1989 | Hasegawa et al. | |
| 4,911,148 A | 3/1990 | Sosnowski et al. | |
| 4,918,521 A | 4/1990 | Yabe et al. | |
| 5,089,895 A | 2/1992 | Fraker et al. | |
| 5,176,126 A | 1/1993 | Chikama | |
| 5,193,525 A | 3/1993 | Silverstein et al. | |
| 5,376,960 A | 12/1994 | Wurster | |
| 5,379,756 A | 1/1995 | Pileski et al. | |
| 5,418,566 A | 5/1995 | Kameishi | |
| 5,438,975 A | 8/1995 | Miyagi et al. | |
| 5,547,457 A | 8/1996 | Tsuyuki et al. | |
| 5,830,401 A | 11/1998 | Prichard et al. | |
| 5,966,168 A | 10/1999 | Miyazaki | |
| 6,004,263 A | 12/1999 | Chi | |
| 6,110,104 A | 8/2000 | Suzuki et al. | |
| 6,302,616 B1 | 10/2001 | Takahashi | |
| 6,456,863 B1 | 9/2002 | Levin et al. | |
| 7,455,806 B2 | 11/2008 | Junger et al. | |
| 7,758,495 B2 | 7/2010 | Pease et al. | |
| 8,029,438 B2 | 10/2011 | Hagihara et al. | |
| 8,182,422 B2 | 5/2012 | Bayer et al. | |
| 8,381,728 B2 | 2/2013 | Rao et al. | |
| 8,547,424 B2 | 10/2013 | Ishii et al. | |
| 8,790,250 B2 | 7/2014 | Petersen et al. | |
| 9,125,582 B2 | 9/2015 | Petersen | |
| 9,220,400 B2 | 12/2015 | Petersen | |
| 9,486,595 B2 | 11/2016 | Borrye et al. | |
| 9,572,482 B2 | 2/2017 | Lin | |
| 9,622,649 B2 | 4/2017 | Lin | |
| 10,182,707 B2 * | 1/2019 | Kirma | A61B 1/00073 |
| 10,321,804 B2 | 6/2019 | Jacobsen et al. | |
| 2002/0022765 A1 | 2/2002 | Belson | |
| 2003/0056540 A1 | 3/2003 | Mukasa et al. | |
| 2004/0143276 A1 | 7/2004 | Sturtz et al. | |
| 2004/0199052 A1 | 10/2004 | Banik et al. | |
| 2004/0242963 A1 | 12/2004 | Matsumoto | |
| 2005/0070759 A1 | 3/2005 | Armstrong | |
| 2005/0075538 A1 | 4/2005 | Banik et al. | |
| 2005/0131279 A1 | 6/2005 | Boulais | |
| 2005/0136217 A1 | 6/2005 | Barthlott et al. | |
| 2005/0140068 A1 | 6/2005 | Junger et al. | |
| 2005/0154262 A1 | 7/2005 | Banik et al. | |
| 2005/0119527 A1 | 9/2005 | Ellis et al. | |
| 2005/0203341 A1 | 9/2005 | Welker et al. | |
| 2005/0234499 A1 | 10/2005 | Olson et al. | |
| 2006/0178556 A1 | 8/2006 | Hasser et al. | |
| 2007/0049800 A1 | 3/2007 | Boulais | |
| 2007/0129466 A1 | 6/2007 | Kagawa et al. | |
| 2007/0249896 A1 | 10/2007 | Goldfarb et al. | |
| 2007/0249907 A1 | 10/2007 | Boulais | |
| 2008/0078386 A1 | 4/2008 | Feldhahn et al. | |
| 2008/0194911 A1 | 8/2008 | Lee | |
| 2008/0221393 A1 | 9/2008 | Padget | |
| 2008/0228035 A1 * | 9/2008 | Hagihara | A61B 1/127 600/176 |
| 2008/0249483 A1 | 10/2008 | Slenker | |
| 2008/0268559 A1 | 10/2008 | Jung | |
| 2008/0287741 A1 | 11/2008 | Ostrovsky | |
| 2009/0054728 A1 | 2/2009 | Trusty | |
| 2009/0093679 A1 | 4/2009 | Suigetsu | |
| 2009/0177040 A1 | 7/2009 | Lyons | |
| 2009/0209819 A1 | 8/2009 | Kitagawa et al. | |
| 2010/0210905 A1 | 8/2010 | Takeuchi et al. | |
| 2010/0217082 A1 | 8/2010 | Ito et al. | |
| 2010/0262180 A1 | 10/2010 | Danitz et al. | |
| 2010/0280316 A1 | 11/2010 | Dietz et al. | |
| 2010/0324367 A1 | 12/2010 | Matsumoto et al. | |
| 2011/0034771 A1 | 2/2011 | Konstorum | |
| 2011/0230718 A1 | 9/2011 | Akui | |
| 2011/0251519 A1 | 10/2011 | Romoscanu | |
| 2012/0029281 A1 | 2/2012 | Frassica et al. | |
| 2012/0165608 A1 | 6/2012 | Banik et al. | |
| 2013/0175720 A1 * | 7/2013 | Otsuka | G02B 23/243 264/1.32 |
| 2013/0245376 A1 | 9/2013 | Masatoshi | |
| 2013/0266761 A1 | 10/2013 | Ho et al. | |
| 2014/0114129 A1 | 4/2014 | Peh | |
| 2014/0182587 A1 | 7/2014 | Dunne et al. | |
| 2014/0200466 A1 | 7/2014 | Sereno et al. | |
| 2014/0276407 A1 * | 9/2014 | DeVries | A61B 18/16 604/103.08 |
| 2014/0318657 A1 | 10/2014 | Bixler et al. | |
| 2015/0251201 A1 | 9/2015 | Hradetzky et al. | |
| 2015/0289751 A1 * | 10/2015 | Frerck | A61B 1/127 264/293 |
| 2015/0306813 A1 | 10/2015 | Roehrig et al. | |
| 2015/0366436 A1 | 12/2015 | Iuel | |
| 2016/0101254 A1 | 4/2016 | Hansen | |
| 2016/0229095 A1 | 8/2016 | Mori et al. | |
| 2016/0287058 A1 | 10/2016 | Ye et al. | |
| 2017/0028684 A1 | 2/2017 | Imai et al. | |
| 2017/0095242 A1 * | 4/2017 | Milbocker | A61B 17/0218 |
| 2017/0146453 A1 * | 5/2017 | Giles | A61B 1/0017 |
| 2019/0016084 A1 | 1/2019 | Hayashi et al. | |
| 2019/0282070 A1 | 9/2019 | Vilhelmsen et al. | |

OTHER PUBLICATIONS

Extended search report in related EP application No. 19199924.2, dated Feb. 14, 2020.

* cited by examiner

TIP PART FOR AN ENDOSCOPE AND THE MANUFACTURE THEREOF

CROSS-REFERENCE TO RELATED APPLICATIONS

This application claims the benefit of, and priority from, European Patent Application No. 19199924.2, filed 26 Sep. 2019, which is incorporated herein by reference in its entirety.

TECHNICAL FIELD

The present disclosure relates to endoscopes, in particular disposable insertion endoscopes, and more specifically but not exclusively to a housing of an insertion endoscope.

BACKGROUND

Endoscopes, which in this context also comprises endotracheal tubes provided with a camera as well as laryngoscopes provided with a camera, are well known devices for visually inspecting inaccessible places such as human body cavities. Endoscopes include insertion endoscopes and capsule endoscopes. Capsule endoscopes are capsules which are normally administered orally and pass through the digestive system. Insertion endoscopes on the other hand are inserted into the body via suitable openings, be it natural or purpose-provided. Insertion endoscopes typically comprise an elongated insertion tube with a handle at the proximal end, as seen from the operator, and visual inspections means, such as a built-in camera, at the distal end of the elongated insertion tube. Electrical wiring for the camera and other electronics such as LED lighting accommodated in the tip part at the distal end run along the inside of the elongated insertion tube from the handle to the tip part. Instead of using cameras, endoscopes may also be fibre-optic, in which case the optical fibres run along inside of the elongated insertion tube to the tip part.

In order to be able to manoeuvre the endoscope inside the body cavity, the distal end of the endoscope may comprise a bending section with increased flexibility, e.g. a number of articulated segments of which the tip part forms the distalmost segment. This is typically done by tensioning or slacking pull wires also running along the inside of the elongated insertion tube from the tip part through the remainder of articulated segments to a control mechanism of the handle. Furthermore, a working channel may run along the inside of the insertion tube from the handle to the tip part, e.g. allowing liquid to be removed from the body cavity or allowing the insertion of surgical instruments or the like into the body cavity.

Modern endoscopes are typically equipped with a least one camera or similar image capturing device at the distal tip of the endoscope. i.e. located within the distalmost segment of the bending section. Provided that sufficient light is present, this allows the operator to see where the endoscope is steered and to set the target of interest once the tip has been advanced thereto. This therefore normally requires illumination of the area in front of the distal tip of the endoscope, in particular the field of vision of the camera(s). One known way of achieving such illumination is to provide the above mentioned LED lighting using one or more Light Emitting Diodes (LEDs) in the tip of the endoscope, as e.g. mentioned in WO2014/106511 disclosing a disposable endoscope.

However, for the camera to see anything the camera lens or any transparent window in front of the camera lens needs to be kept clean, i.e. free of objects interfering with the passage of light, e.g. liquids and/or particulate matter. In this respect it has been suggested to provide a microscopic or nanoscopic coating on the transparent window, be it a separate window or a window formed directly by a camera lens part, or even a window of a covering sheath for an endoscope, as inter alia suggested in US2015/0289751. This microscopic or nanoscopic coating may provide the transparent window with hydrophobic properties, allowing it to have self-cleaning properties, as the impurities that may obstruct vision will be repelled away together with the liquid in which they are suspended. A similar idea is disclosed for a capsule endoscope in US2016/0287058.

Providing these coatings in an optically sufficient quality, is however not unproblematic, in particular if, as is the case for disposable endoscopes, the manufacturing costs are to be kept very low.

SUMMARY

On this background it is the object to provide an endoscope, preferably, a disposable insertion endoscope, with good self-cleaning properties and low costs. In this respect the inventors have now realized that good self-cleaning properties may be achieved even if a hydrophobic microstructure or nanostructure is not provided on the window itself.

Thus, according to a first aspect of the disclosure, the object is achieved by a tip part for an endoscope, said tip part having at least one transparent part and at least one opaque part providing an outer surface, comprising a transparent outer surface part and an opaque outer surface part, respectively, wherein the transparent outer surface part is smooth, i.e. without any well-defined nanostructure or microstructure, and wherein at least a part of the opaque outer surface part is provided with a hydrophobic structure.

According to a second aspect of the disclosure, the object is achieved by a method for the manufacture of a tip part of an endoscope according to the first aspect of the disclosure, wherein the at least one transparent part and the at least one opaque part are provided as an integral one-piece body by two-stage two-component injection moulding.

According to a third aspect of the disclosure the object is achieved by a disposable insertion endoscope with a tip according to the first aspect of the disclosure and embodiments thereof.

Providing the hydrophobic structure on the opaque parts only and not on the transparent parts will allow the hydrophobic structure to be coarser (i.e. larger dimensions) than what would be acceptable if it was provided on the transparent part too, because there are no optical effects to be taken into account. That is to say, if the hydrophobic structure were to be provided on the transparent part the features of the hydrophobic structure would need to be a nanostructure, i.e. having features below the wavelengths of visible light, so as to not influence the light passing the surface. Instead the hydrophobic structure may be provided as a microstructure, which is easier and cheaper to manufacture.

According to a first embodiment of the first aspect of the disclosure the part of the opaque outer surface part which is provided with a hydrophobic structure is located adjacent the transparent part. These are the areas where the hydrophobic properties do the most benefit. As long as the area of hydrophobic structure is large enough, the remainder of the opaque material of the tip part need not have a hydrophobic structure.

This is, in particular, the case in another preferred embodiment of the first aspect of the disclosure, wherein the hydrophobic structure is located on the front face only. This suffices, and from a manufacturing perspective advantageous in that it becomes easier to extract the housing of the tip part or the whole tip part itself, as the case may be, from a mould without damaging the microstructure or nanostructure providing the hydrophobic structure.

This in turn is advantageous if, according to a further preferred embodiment of the first aspect of the disclosure, the hydrophobic structure is provided directly in the surface of the opaque outer surface part.

According to another preferred embodiment of the first aspect of the disclosure, the hydrophobic structure is or comprises a microstructure. This is advantageous as, from a manufacturing perspective, a microstructure is easier and cheaper to provide as compared to a nanostructure.

According to a specific preferred embodiment for the first aspect of the disclosure, the distance between repeated features is less than 2 μm, preferably in the range between 50 nm to 2 μm. This suffices to give good hydrophobic properties, while still being easy to manufacture.

According to a further preferred embodiment of the first aspect of the disclosure the hydrophobic structure comprises a nanostructure, more specifically a nanostructure, wherein the distance between repeated features is less than the longest wavelength of visible light, preferably less than 380 nm, and more preferably in the range from 200 nm to 300 nm. This may provide good hydrophobic properties, but it may also provide the microstructure with additional desirable properties. This is in particular the case when, according to yet a further preferred embodiment the nanostructure is superimposed on the microstructure.

According to yet a further preferred embodiment of the first aspect of the disclosure, the distal front face comprises at least two transparent outer surface parts, which on the front face are separated by an opaque outer surface part provided with the hydrophobic structure. Experience has shown that the cleaning effect of the hydrophobic structure is improved when the hydrophobic structure is located between smooth transparent areas which, in comparison with the opaque area with the hydrophobic structure, have a smaller area.

According to a first preferred embodiment of the second aspect of the disclosure the transparent part is moulded in a transparent part mould cavity, and wherein the opaque part is moulded in an opaque part mould cavity, said opaque part mould cavity comprising a structured inner surface, adapted to provide the opaque part with hydrophobic properties. This allows optimisation of the moulding process with respect to injection pressures and the like for the different materials and their different material properties, e.g. if the transparent material is more brittle than the opaque material.

Thus, according to a further preferred embodiment of the second aspect of the disclosure, the transparent part is moulded in a first step, and the opaque part is moulded in a subsequent second step. Thus, the typically more brittle transparent material may be moulded at a suitable injection pressure for reducing flaws from shrinking and suction of the material in the moulding process.

Two-stage two-component injection moulding is, in particular, of advantage when, according to a further preferred embodiment of the second aspect of the disclosure the integral body is a cup-shaped housing.

This however does not exclude that according to another embodiment of the disclosure, the hydrophobic structure is a nanostructure.

BRIEF DESCRIPTION OF THE FIGURES

The invention will now be described in greater detail, based on non-limiting exemplary embodiments and with reference to the drawings on which.

DETAILED DESCRIPTION

Figure 1:
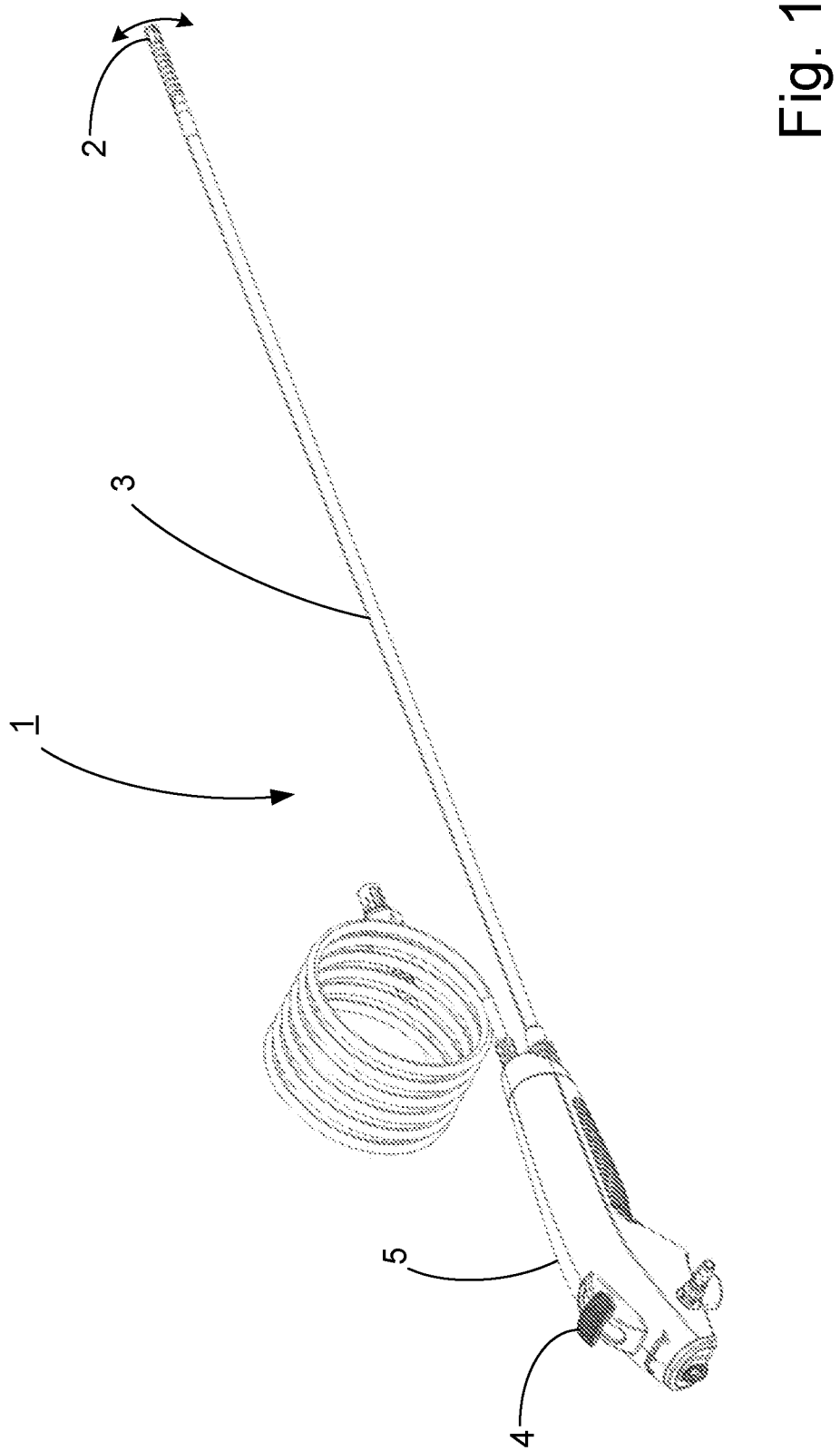
FIG. 1 shows an embodiment of a disposable insertion endoscope with a tip part.

Turning first to FIG. 1, a disposable insertion endoscope 1 with a tip part 2 according to the disclosure at the end of the insertion tube 3 is shown. The tip part 2 in the embodiment shown forms the distalmost segment of a bending section which may be moved in a bidirectional motion as indicated by the double arrow. This bidirectional motion is effected by manual control of a lever 4 arranged at the handle 5 of the endoscope 1. The tip part 2 typically has a cylindrical shape. The tip part 2 may be provided in many different ways, e.g. as a generally cup shaped housing containing the various parts such as an illumination means, a camera, electronics, wires, and the terminal end of the control cables or pull wires from the lever 4. Another way would be to embed the components in a suitable plastic material, by moulding the plastic material around them in a suitable mould corresponding to the e.g. cylindrical outer shape of the tip part 2.

Figure 2:
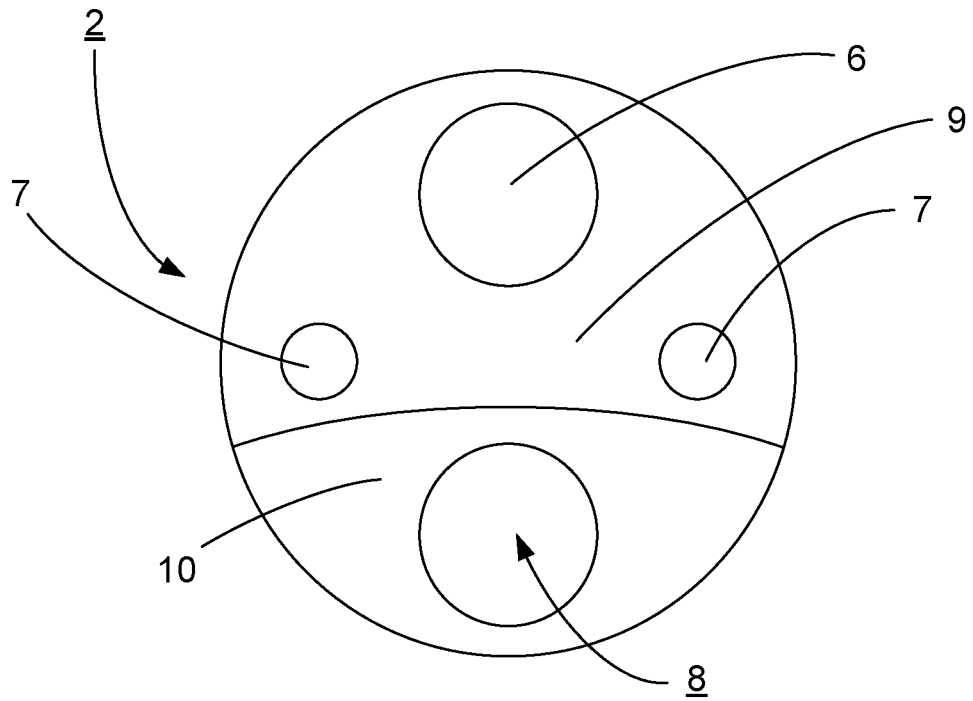
FIG. 2 shows an embodiment of a front face of the tip part of FIG. 1.
Figure 3:
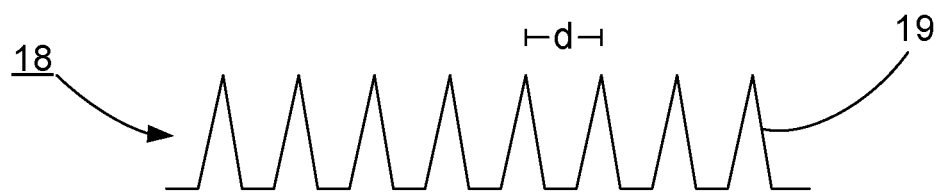
FIGS. 3 to 9 show various geometries of embodiments of hydrophobic structures.

Turning now to FIG. 2 the front view of the distal end of the tip part 2 is shown. In the front view a first transparent part 6 can be seen. Depending on the embodiment this may be the outermost camera lens or window of a camera. In another embodiment the transparent part may be a smooth window part forming part of the housing and arranged in front of a camera in the housing. Furthermore, two second transparent parts 7 can be in the front view. Depending on the embodiment these could be the ends of optical fibres, light guides, or LEDs. Alternatively, they could be smooth transparent windows arranged in front of such ends of optical fibres, light guides, or LEDs. In this context smooth is to be understood as free of any well-defined nanostructure or microstructure.

Typically, the front end would also comprise an opening 8 forming the open end of a working channel running through the insertion tube 3.

As mentioned, at least a part of the area of the front face may be provided with a hydrophobic structure. Preferably, at least a first area 9 adjacent and in the illustrated example entirely surrounding both of the first and second transparent parts 6, 7, is thus provided with such a hydrophobic structure. Though illustrated as one contiguous surface, the surfaces with the hydrophobic structure could be disjunct, i.e. separate hydrophobic structures adjacent each individual transparent part 6, 7. In the illustrated example a second part 10 of the opaque part of the front face is left free of hydrophobic structure, but this of course need not be so. The entire opaque part of the front surface as well as the surrounding mantle surface of the normally cylindrical tip part could also be provided with a hydrophobic structure.

A non-limiting selection of examples of hydrophobic structures 18 according to the disclosure are illustrated in FIGS. 3 to 8.

The tip part 2 has a housing (see e.g. FIGS. 10-12) having a proximal end opposite a distal end and an outer peripheral surface extending between the proximal end and the distal end. The housing also has an outer distal surface at the distal end. The camera is positioned in the housing and has an optical axis. The housing includes a camera viewing area that is transparent and traversed by the optical axis. The housing also includes a textured area surrounding the camera viewing area. The textured area comprises a first regulated pattern of outwardly extending protrusions. The protrusions extend from a plane on the housing's outer surface (peripheral or distal) and extend outwardly, either radially from the peripheral surface or distally from the distal surface. Generally, the axis of each protrusion may extend substantially in parallel with the viewing angle of the camera. The viewing angle may be substantially axial in a distally-facing camera or substantially radial in a laterally-facing camera, such as in a duodenum endoscope. Examples of first regulated patterns are discussed with reference to FIGS. 2-9.

The first transparent part 6 may be a part or a portion of the housing formed in a single-piece with other portions of the housing, as described below and may comprise the camera viewing area. The second transparent part 7 may be a part or a portion of the housing formed in a single-piece with other portions of the housing and may comprise a light transmission area to enable light transmission from a light source positioned in the housing. The textured area may surround the light transmission area. The textured area may be located between the camera viewing area and the light transmission area, e.g. between the first and second transparent parts 6, 7. The outer distal surface of the housing or the outer peripheral surface of the housing may comprise the camera viewing area and the textured area. The textured area may comprise a second regulated pattern of outwardly extending protrusions disposed between the outwardly extending protrusions of the first regulated pattern. The textured area may comprise first and second regulated patterns, each with repeating features spaced at least 200 nm, while the camera viewing area and the light transmission area are devoid of regulated patterns, e.g. devoid of repeating patterns formed to provide hydrophobicity.

Figure 4:
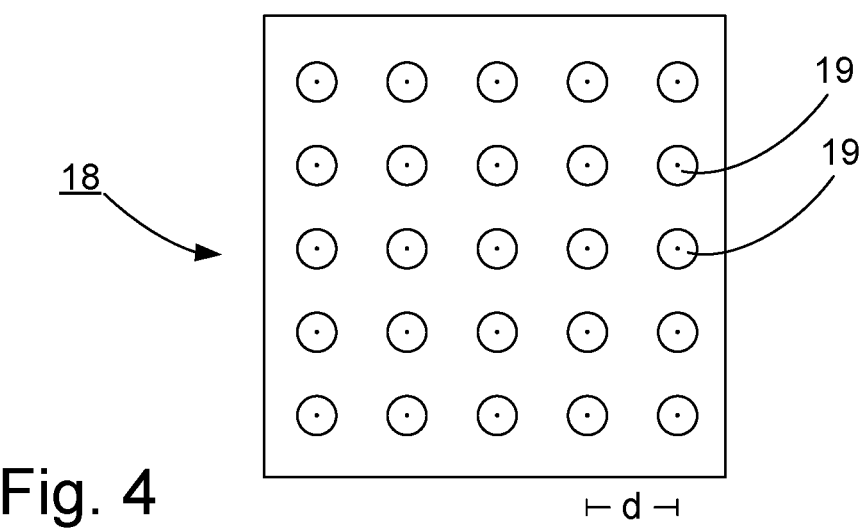
Figure 5:
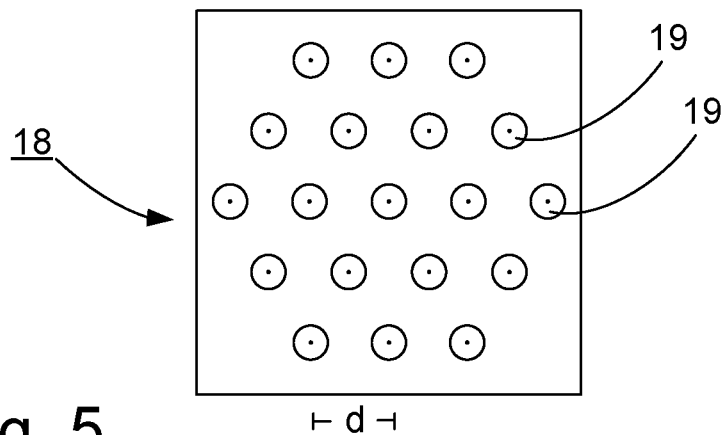
Figure 6:
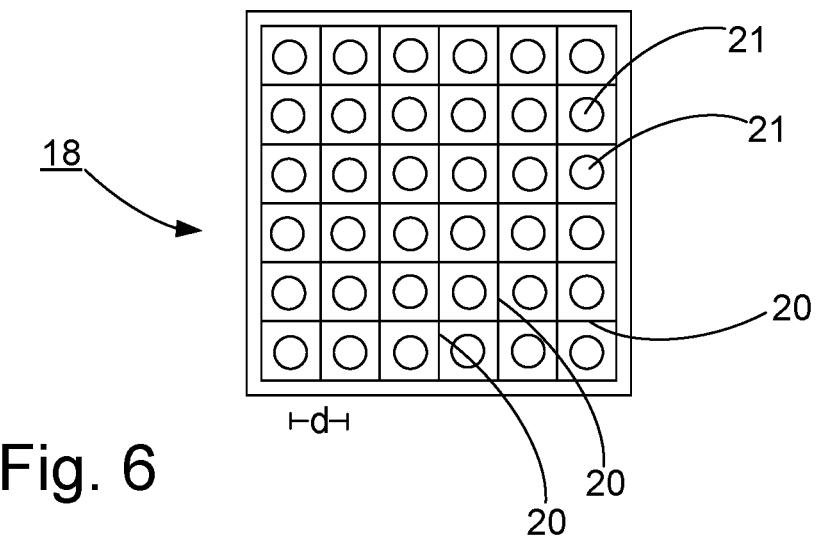
Figure 7:
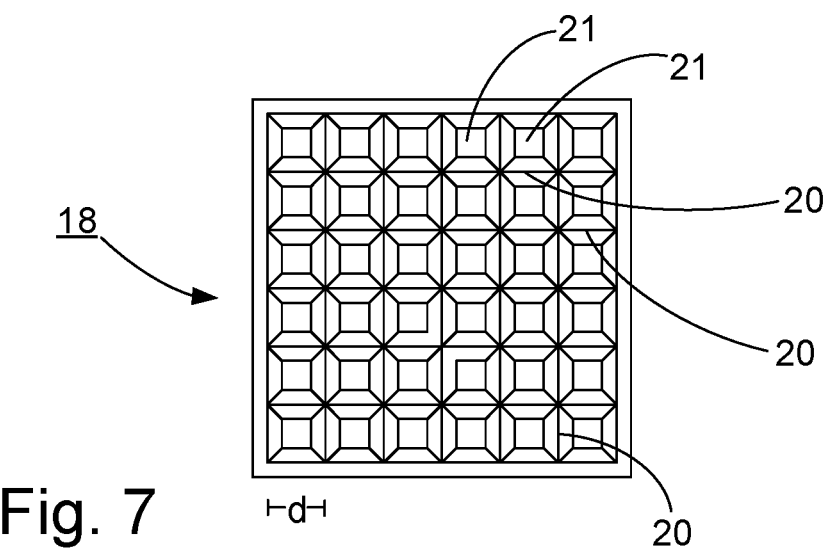

As can be seen in FIGS. 3 to 8 the hydrophobic structure 18 comprises features 19, 20, 21 extending generally perpendicular from the overall plane of the surface, i.e. from the opaque surface areas 9, 10 of the front face. The surfaces are preferably smooth except for the features 19, 20, 21 and plane, the plane of the surface preferably extending transversely to the optical axis of the camera of the camera assembly and/or to the illumination device 14. If the smooth surface of the transparent parts 6, 7 are plane, they may preferably extend in the same plane as the opaque surface areas 9, 10. The features of FIG. 3, as can be seen, are preferably identical elements such as peaks 19 in the shape of cones or pyramids arranged in predetermined patterns in one or two dimensions. In the simplest form the pattern consists in the peaks being equidistant in one predetermined direction, as shown schematically in FIG. 3. Of course, because an area has to be covered, the pattern will normally also be repetitive in a second dimension as illustrated in FIG. 4, where cones are arranged in a square grid manner, where a fourth order symmetry is provided. Another pattern with sixth order symmetry, i.e. a hexagonal pattern is illustrated in FIG. 5 but as the skilled person will realize there are numerous patterns where the features are repetitive and/or where neighbouring features are equidistant. This does not limit itself to cones 19 or pyramids, but includes ribs or ridges 20 separated by valleys if the ribs or ridges 20 are in parallel or concentric, or pits 21, if as illustrated in FIGS. 6 and 7, the ridges 20 cross each other.

Often, however, peaks in the shape of cones are preferred. These are preferably arranged in hexagonal patterns as illustrated in FIG. 5 where the spacing d from a given cone to all six neighbouring cones is the same.

The distance d will depend on the properties desired for the front surface 15. If only hydrophobic properties are desired, the spacing d from one peak to the closest adjacent peak should preferably be less than 2 μm, preferably in the range from 50 nm to 2 μm.

If, additionally, anti-glare properties are also desired, the spacing d between the features should be less than wavelengths of visible light. Thus, the spacing d between the features is preferably less than 380 nm, preferably in the range from 200 nm to 300 nm. In this description such features with spacing d smaller than the wavelengths of visible light are referred to as nano-structures.

The height of the features will typically be approximately the same as the spacing d between them, or at least in the same order of magnitude, e.g. a height in the range of ½d to 2d, i.e. half to twice the spacing d.

Please, note that since the patterns of the micro-structures and nano-structures may be identical except for their dimensions, the spacing is generally termed d and in cases where distinction is necessary the d relating to the nano-structure is substituted with d'.

It should be noted that under certain circumstances it is in fact possible to superpose two different micro and/or nano-structures 18. That is to say if the spacing d', the features and/or the pattern characterizing the anti-glare properties and the spacing d, the features and/or the pattern solely characterizing the hydrophobic properties differ sufficient to not disturb each other they can be provided in the same area. If, as an example, the hexagonal structure of FIG. 5 is laid out with a spacing d of 2 μm between cones, there will be plenty of space between those cones 19 for other features, e.g. smaller cones 19 with a smaller spacing of e.g. 200 nm.

Figure 8:
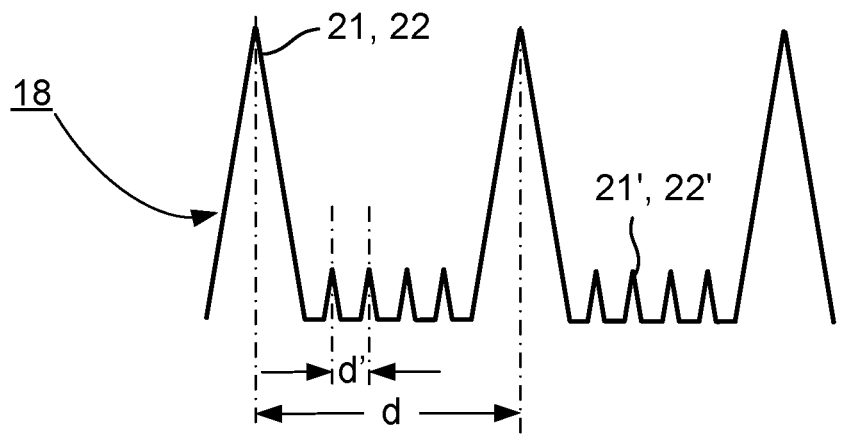

FIG. 8 illustrates an example of the first regulated pattern 22 comprising protrusions 21 and the second regulated pattern 22', embedded in the first regulated pattern 22, comprising protrusions 21'. This arrangement may provide both hydrophobicity and anti-glare properties to the housing.

Figure 9:
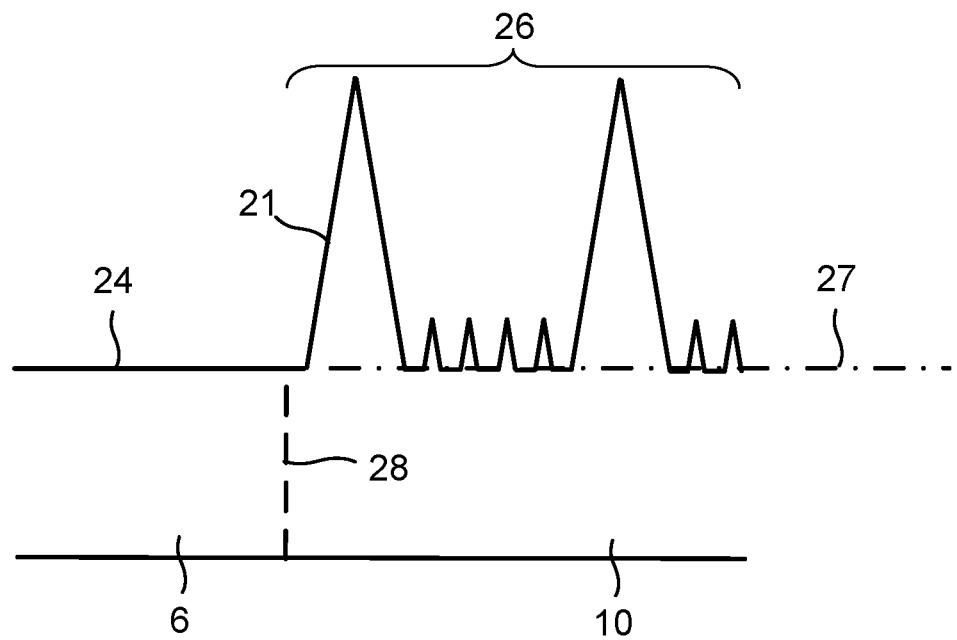

FIG. 9 depicts the first regulated pattern 22 and the second regulated pattern 22' providing a textured area 26 surrounding the camera viewing area 24. Of course the second regulated pattern 22' may be omitted from the textured area 26. As shown, protrusions, or features, 21 extend from a plane 27 of the outer surface of the housing. The outer surface comprising the camera viewing area 24 may be on the same plane 27 or may be on a different plane, depending on how it is manufactured. Plane 27 may coextend or be placed more outwardly than camera viewing area 26 to enhance the function provided by the hydrophobicity and thus keep the camera viewing area 26 more unobstructed than it would be otherwise. The figure also depicts the transparent outer surface part 6 and the opaque outer surface part 10, with a surface 28 therebetween at which the parts are mated.

In a preferred embodiment, the tip part itself or the housing there of is a two-component moulded tip, e.g.

moulded integrally from a transparent and an opaque material in one single moulding process. In such embodiments, the hydrophobic structure 18 is preferably provided directly in the surface in the moulding process, but may be provided later in a stamping process, e.g. by heating the polymer material to make it soft plastic again and stamping it with a suitably structured stamp. In either case the hydrophobic structure is ready to use and does not require any further treatment, such as chemical hydrophobic coatings or coatings with nanoparticles.

As to the manufacturing process, when according to one embodiment the housing is a separate cup-shaped housing it is preferably made by injection moulding of one or more suitable polymer materials. That is to say the entire housing may be manufactured by injection moulding using material injected into a single mould cavity with an external shape matching the desired exterior of the housing. In that case the housing will comprise a circumferential wall and a bottom formed integrally as a single piece from one and the same material. For a generally cup-shaped housing where the circumferential wall is cylindrical, the external shape of the mould cavity would be a cylindrical cavity with a generally flat bottom, save for the areas with the hydrophobic structure 18 and possibly the working channel passage 8 and convex or concave window or lens parts 6, 7. The working channel 8 could of course also be provided by the counterpart of the mould cavity, or if necessary by suitable inserted cores.

To provide the hydrophobic structure 18, the bottom of the mould cavity is preferably lined with an interchangeable prefabricated shim with engraved, etched or otherwise imprinted with a negative of the desired hydrophobic structure 18. An example of a process for making such a shim, and a corresponding nano-structure, is disclosed in the document "Injection moulding of antireflective nanostructures", Christensen, A. B. et al, DTU Orbit, 2013, available from URL: <http://orbit.dtu.dk/files/97131108/AlexanderBC_MNE2013_poster.pdf>. In this document a master pattern corresponding to the desired structure, in casu a nano-structure, is etched in black silicon. A nickel shim is then provided by electroplating the black silicon. The nickel shim subsequently coated with an anti-stick coating. The coated nickel shim is placed in a mould and an item with a nano-structure providing an anti-reflective surface is then injection moulded from a black polymer. The suggestion is made that this may be useful for replacing anti-reflective coatings for camera objectives and other glass items. However, the inventors have realized that this may also be used to provide hydrophobic properties, to non-transparent areas. An inverse structure for a stamp, used to imprint the hydrophobic structure could be prepared as a shim in a similar manner.

The opaque material may be selected from various types of polymers, such as thermoplastic, thermosetting plastic, or silicone. The latter could be advantageous in that it can be injected as a low viscosity liquid, well able to enter into the fine details of the shim before setting to form the hydrophobic structure 18 directly in the material of the front wall 3. Silicone would have the further advantage of having also inherent hydrophobic properties. Other useful polymers would be PC, COC, COP, PMMA or ASA, and the skilled person will readily be able to identify further polymers and fillers having suitable properties in terms of e.g. biocompatibility, mechanical strength, brittleness, lack of transparency, adhesiveness, etc.

In respect of allowing the polymer to enter into the fine details of the hydrophobic structure of the mould it may be of advantage to apply vacuum to the mould in order to avoid air being trapped in the fine hydrophobic structure and hindering the proper ingress of the polymer material.

Rather than making the housing from one single material, it may also be made from two or more materials with different material properties, one of which obviously being transparent in order to form the transparent front areas 6 or windows matching the locations of the camera and the illumination device (or devices) 7, respectively. The other material or materials may be optimised for other properties such as compatibility with adhesives, opaqueness, resiliency, etc. As can be seen from FIG. 2 an example of a preferred embodiment has transparent front face windows 6, 7 made from a material different from the opaque areas 9, 10 with the hydrophobic structure surrounding the front face windows. The opaque could also have good adhesive properties in order to secure a sealing outer sheath to the cylindrical mantle face i.e. the circumferential wall (omitted in FIG. 1 for illustration purposes) of the insertion tube 3 of the endoscope to the housing of the tip, or for adhering to a sealing material serving as a closure of the housing to protect the electronic components.

The housing according can be made in a two-component moulding process, where in a first stage the transparent parts are first moulded in a first mould cavity closed by a closure part. The moulded transparent parts are then moved on the closure part to a second mould cavity slightly larger than the first mould cavity in order to provide a mould cavity corresponding to the front face and the circumferential wall. This second mould cavity in that case being lined, at least at the bottom with the shim carrying the complementary hydrophobic structure. Then in a second moulding step the opaque polymer material of front wall is injected and sets to form the front wall with the hydrophobic structure 18 in the front face. In the second stage of the process a higher injection pressure may be used as compared to the first stage, in order to secure proper ingress of the material into the complementary hydrophobic structure of the shim, thus forming the hydrophobic structure directly in the material of the front wall.

It is of course not excluded to first mould the opaque part in the first stage of the two-stage two-component moulding process and subsequently in the second stage the transparent part, e.g. in order to avoid internal tensions in the transparent material, that could deteriorate the optical properties thereof.

It should be noted that the use of nickel shim is not the only way of providing the complementary hydrophobic structure, it may be formed in other materials or even directly in the wall of the mould cavity in which the front wall is moulded.

It should also be noted that injection moulding of a cup-shaped housing for the components is not the only way to provide such a housing. It is also possible to mould-in electronic and transparent components in an opaque material by placing the components in a mould, and pouring a suitable plastic material into the mould, as known from EP2387346A, incorporated herein by reference. In that case a suitable inverse pattern corresponding to the desired hydrophobic structure is to be arranged in a suitable place in the mould e.g. in the bottom. This inverse hydrophobic structure, in turn, could be as an imprint directly in the bottom of the mould or could be provided as a loose, and preferably interchangeable, shim as described above placed in the bottom of the mould.

Figure 10:
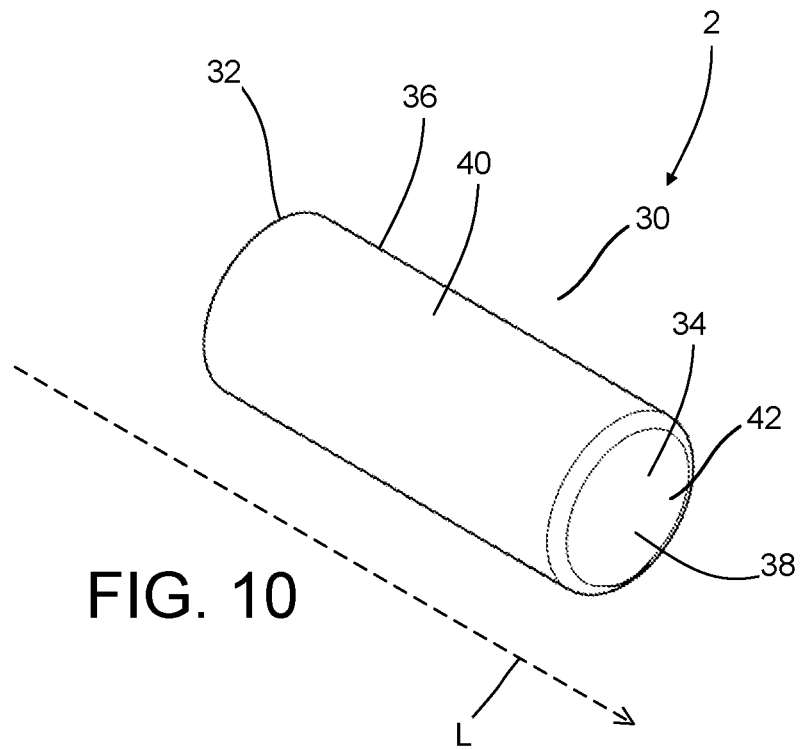
FIGS. 10 to 12 show various embodiments of housings of the tip part.
Figure 11:
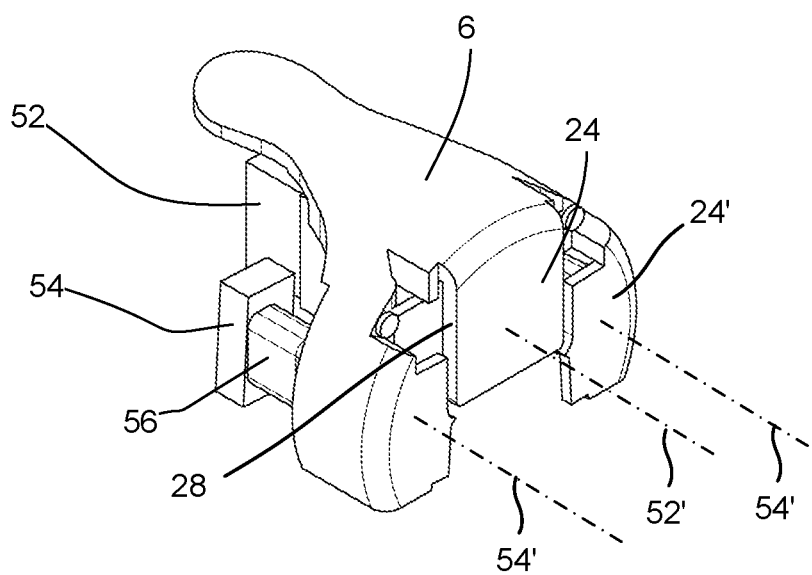

FIGS. 10 and 11 illustrate an embodiment of a housing 30 of the tip part 2, as described above, having a proximal end 32 opposite a distal end 34 and an outer peripheral surface 40 extending between the proximal end and the distal end and provided by a peripheral wall 36. The longitudinal axis of the housing 30 is depicted as L, in the proximal-distal direction. The housing also has an outer distal surface 42 provided by a distal wall 38, at the distal end 34. The camera 52 is positioned in the housing and has an optical axis or viewing angle 52'. The light source or illumination means 54 is positioned in the housing and has a light emission axis or angle 54'. Obviously light is emitted in a broad range of angles and not merely along the emission axis. A light guide 56 is also shown. The housing includes a camera viewing area 24 that is transparent and traversed by the optical axis. The housing also includes a textured area surrounding the camera viewing area. In FIG. 11 only the transparent outer surface part 6 is shown, having surface 224, 24'. The opaque outer surface part 10 complements the shape of the transparent outer surface part 6 to form the cylindrical housing 30. The first transparent part 6 in the present embodiment is mated to form a single-piece housing with the second transparent part 7.

Figure 12:
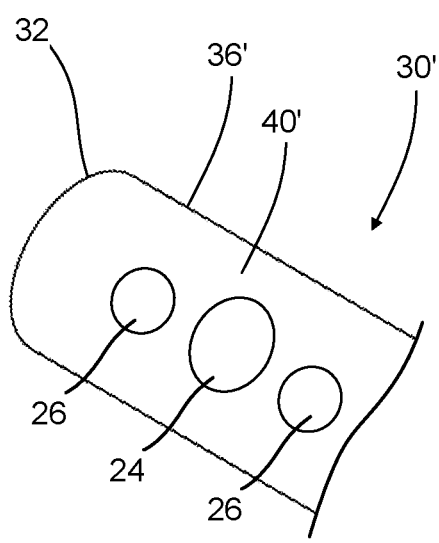

The viewing angle may be substantially axial in a distally-facing camera, as shown in FIG. 11, or substantially radial in a laterally-facing camera, such as in a duodenum endoscope. An embodiment of a laterally-facing camera is shown in FIG. 12. There, a housing 30' of the tip part 2 is shown having an outer peripheral surface 40' extending between the proximal end and the distal end and provided by a peripheral wall 36'. The distal end of the housing 30' is not shown but in a duodenum endoscope typically includes an elevator bar and other known features.

Additional embodiments and examples include the following:

[1] A tip part for an endoscope, said tip part having at least one transparent part and at least one opaque part providing an outer surface, comprising a transparent outer surface part and an opaque outer surface part, respectively, wherein the transparent outer surface part is smooth, and wherein at least a part of the opaque outer surface part is provided with a hydrophobic structure.

[2] A tip part according to [1], wherein the part of the opaque outer surface part which is provided with a hydrophobic structure is located adjacent the transparent part.

[3] A tip part according to any one of [1] or [2], wherein the hydrophobic structure is located on the front face only.

[4] A tip part according to any one of [1] to [3], wherein the hydrophobic structure is provided directly in the surface of the opaque outer surface part.

[5] A tip part according to any one of [1] to [4], wherein the hydrophobic structure comprises a microstructure.

[6] A tip part according to [5], wherein the distance d between repeated features is less than 2 μm, preferably in the range between 50 nm to 2 μm.

[7] A tip part according to any one of [1] to [6], wherein the hydrophobic structure comprises a nanostructure.

[8] A tip part according to [7], wherein the distance d' between repeated features is less than the longest wavelength of visible light, preferably less than 380 nm, and more preferably in the range from 200 nm to 300 nm.

[9] A tip part according [6], wherein a nanostructure according to one of claim 7 or 8 is superimposed on the microstructure.

[10] A tip part according to any one of [1] to [9], wherein the distal front face comprises at least two transparent outer surface parts, which on the front face are separated by an opaque outer surface part provided with the hydrophobic structure.

[11] A method for the manufacture of a tip part of an endoscope according to any one of [1] to [10], wherein the at least one transparent part and the at least one opaque part are provided as an integral body formed in a single-piece by two-stage two-component injection moulding.

[12] A method according to [11], wherein the transparent part is moulded in a transparent part mould cavity, and the opaque part is moulded in an opaque part mould cavity, said opaque part mould cavity comprising a structured inner surface, adapted to provide the opaque part with hydrophobic properties.

[13] A method according to [11] or [12], wherein the transparent part is moulded in a first step, and the opaque part is moulded in a subsequent second step.

[14] A method according to any one of [11] to [13], wherein the integral body is a cup-shaped housing.

[15] A disposable insertion endoscope with a tip according to any one of [1] to [10].

We claim:

1. An endoscope comprising:
a bending section;
a tip part including a housing supported by the bending section, the housing having a proximal end opposite a distal end, a distal wall at the distal end comprising an outer distal surface, and an outer peripheral surface extending between the proximal end and the distal end; and
a camera positioned in the housing and having an optical axis,
wherein the distal wall of the housing includes a camera viewing area, a light transmission area separate from the camera viewing area, and an opaque portion at least between the camera viewing area and the light transmission area, the camera viewing area being transparent and traversed by the optical axis, and the light transmission area being transparent, and
wherein the opaque portion of the distal wall includes a textured area comprising a first regulated pattern of outwardly extending protrusions, the first regulated pattern comprising a repeating pattern molded or stamped onto the housing to provide hydrophobicity, the repeating pattern comprising features equidistant in at least one predetermined direction.

2. The endoscope of claim 1, wherein a distance d between the extending protrusions is in the range between, and including, 50 nm to 2 μm.

3. The endoscope of claim 2, wherein a distance d between the extending protrusions is in the range between, and including, 200 nm to 300 nm.

4. The endoscope of claim 2, wherein the textured area comprises a second regulated pattern of outwardly extending protrusions disposed between the outwardly extending protrusions of the first regulated pattern, and a distance d' between the outwardly extending protrusions of the second regulated pattern is less than or equal to 740 nm.

5. The endoscope of claim 4, wherein the distance d' between the outwardly extending protrusions of the second regulated pattern is less than or equal to 380 nm.

6. The endoscope of claim 5, wherein the distance d' between the outwardly extending protrusions of the second regulated pattern is in a range from, and including, 200 nm to 300 nm.

7. The endoscope of claim 1, wherein the the camera viewing area is devoid of the first regulated pattern of outwardly extending protrusions.

8. The endoscope of claim 1, wherein a distance d between the extending protrusions is constant and in the range between, and including, 200 nm to 300 μm.

9. The endoscope of claim 1, wherein the opaque portion of the distal wall at least partially surrounds the camera viewing area and the light transmission area.

10. The endoscope of claim 1, wherein the textured area is provided onto the entire opaque portion.

11. A method of making an endoscope, the method comprising:
   injection molding housing having a peripheral wall extending between a proximal end and a distal end of the housing and a distal wall at the distal end, the distal wall having an outer distal surface, and the peripheral wall having an outer peripheral surface;
   providing a textured area by molding or stamping a first regulated pattern onto the outer distal surface at least partly surrounding the camera viewing area, the first regulated pattern comprising a repeating pattern of outwardly extending protrusions molded or stamped onto the housing to provide hydrophobicity, the repeating pattern comprising features equidistant in at least one predetermined direction;
   positioning a camera having an optical axis in the housing to form a tip part; and
   connecting the tip part to a bending section,
   wherein the housing includes a camera viewing area, a light transmission area separate from the camera viewing area, and an opaque portion at least between the camera viewing area and the light transmission area, the camera viewing area and the light transmission area being transparent, and
   wherein the opaque portion comprises the first regulated pattern of outwardly extending protrusions.

12. The method of claim 11, wherein the injection molding comprises molding the outer peripheral wall with the distal wall to form the housing in one-piece.

13. The method of claim 11, further comprising positioning a camera in the housing with an optical axis of the camera traversing the camera viewing area.

14. The method of claim 11, wherein the injection molding comprises molding a transparent portion in a transparent part mould cavity and molding an opaque portion in an opaque part mould cavity comprising a structured inner surface sized and shaped to provide the opaque portion with the first regulated pattern.

15. The method of claim 14, wherein the transparent portion is molded in a first step and the opaque portion is molded in a second step subsequent to the first step.

16. An housing for a tip part of an endoscope, the housing comprising:
   a proximal end;
   a distal end opposite the proximal end;
   a circumferential wall having an outer peripheral surface extending between the proximal end and the distal end; and
   a distal wall at the distal end, the distal wall having an outer distal surface,
   wherein the distal wall includes a camera viewing area, a light transmission area separate from the camera viewing area, and an opaque portion at least between the camera viewing area and the light transmission area, the camera viewing area being transparent and traversed by an optical axis of a camera positioned in the housing during assembly thereof, the light transmission area being transparent, and
   wherein the opaque portion of the distal wall includes a textured area formed on the outer distal surface at least partially surrounding the camera viewing area, the textured area comprising a first regulated pattern of outwardly extending protrusions, the first regulated pattern comprising a repeating pattern molded or stamped onto the housing to provide hydrophobicity, the repeating pattern comprising features equidistant in at least one predetermined direction.

17. The housing of claim 16, wherein a distance d between the extending protrusions is constant and in the range between, and including, 200 nm to 300 μm.

* * * * *